United States Patent [19]

Poole

[11] Patent Number: 5,522,555
[45] Date of Patent: Jun. 4, 1996

[54] DRY POWDER DISPERSION SYSTEM

[75] Inventor: Trent A. Poole, South Amherst, Mass.

[73] Assignee: Amherst Process Instruments, Inc., Hadley, Mass.

[21] Appl. No.: 204,476

[22] Filed: Mar. 1, 1994

[51] Int. Cl.$^6$ ............... B02C 19/06; B02C 21/00; B02C 23/20; B02C 23/38
[52] U.S. Cl. ............... 241/33; 241/39; 241/42; 241/57; 241/60; 241/152.2; 406/14; 406/30
[58] Field of Search ............... 239/399, 403, 239/407, 413; 241/33, 34, 39, 40, 41, 42, 57, 60, 61, 62, 152.2; 406/14, 30

[56] References Cited

U.S. PATENT DOCUMENTS

| | | | |
|---|---|---|---|
| 197,601 | 11/1877 | Cassidy | 222/195 |
| 1,062,306 | 5/1913 | Stobie | 241/5 X |
| 1,614,314 | 1/1927 | Murray et al. | 241/5 X |
| 1,814,560 | 6/1931 | Kreisinger | 241/48 X |
| 2,072,845 | 3/1937 | Benoit | 222/195 |
| 2,153,419 | 4/1939 | Hoffman | 222/4 |
| 2,628,787 | 2/1953 | Payne | 241/39 |
| 2,702,471 | 2/1955 | Vonnegut | 73/28 |
| 2,730,005 | 1/1956 | Vonnegut | 88/14 |
| 2,732,753 | 1/1956 | O'Konski | 88/14 |
| 2,825,872 | 3/1958 | Stubbs et al. | 324/71 |
| 2,932,394 | 4/1960 | McGinn | 209/135 |
| 2,932,966 | 4/1960 | Grindell | 73/28 |
| 2,947,164 | 8/1960 | Orr, Jr. | 73/28 |
| 2,986,923 | 6/1961 | Vonnegut | 73/28 |
| 3,138,029 | 6/1964 | Rich | 73/432 |
| 3,162,379 | 12/1964 | Cohn et al. | 241/5 X |
| 3,208,286 | 9/1965 | Richard | 73/432 |
| 3,220,261 | 11/1965 | Kriebel | 73/432 |
| 3,380,584 | 4/1968 | Fulwyler | 209/3 |
| 3,434,335 | 3/1969 | Langer | 73/28 |
| 3,462,608 | 8/1969 | Weston et al. | 208/218 |

(List continued on next page.)

OTHER PUBLICATIONS

W. J. Yanta et al, "The Use of a Laser Doppler Velocimeter in Supersonic Flow," AIAA Paper No. 71–287, Mar., 1971.
Albert L. Thomas, Jr. et al, "A Portable Photometer and Particle Size Analyzer," ISA Journal, vol. 8, No. 7, Jul. 1961, pp. 52–56.
The APS33 Aerodynamic Particle Sizer Brochure, TSI Incorporated.
D. B. Blackford et al, "Particle Sizer Analysis With an Aerodynamic Particle Sizer", Proceeding of the 11th Annual Powder and Bulk Solids Conf., Rosemont, IL, pp. 615–623, May 12–15, 1986.
J. K. Agarwal et al, "An Instrument for Real Time Aerodynamic Particle Size Analysis Using Laser Velocimetry", Proceeding of The Inhalation, Toxicology and Technology Symp. ed. by Basil K. J. Leong, Ann Arbor Science Publishers, 1981, pp. 207–231.
Rajac, "Surface Particle Analyzer", IBM Bulletin, vol. 22, No. 10, Mar. 1980.

*Primary Examiner*—Timothy V. Eley
*Attorney, Agent, or Firm*—Wolf, Greenfield & Sacks

[57] ABSTRACT

A powder dispersion system, including a powder disperser and a control unit, supplies a controlled particle stream to a particle sizing system, instrument, or other processing device. The powder disperser includes a dynamic shear dispersion assembly and may include a fluidization assembly. An impact surface for deagglomeration of particles is located within a rapid acceleration chamber of the dynamic shear dispersion assembly. The particles are accelerated from the impact surface through an annular nozzle. A feedback loop dynamically controls the dynamic shear force applied to the aerosol transport gas, which in turn places reaction forces upon the particles, within the annular nozzle. The fluidization assembly includes a primary chamber for holding a powder sample and a secondary chamber for entraining particles of the powder sample in a transport gas stream. A pulsed gas jet directed into the primary chamber disperses particles of the powder sample into the secondary chamber. Particles are transported from the secondary chamber to the dynamic shear dispersion assembly through a controlled velocity momentum tube.

48 Claims, 8 Drawing Sheets

U.S. PATENT DOCUMENTS

| | | | |
|---|---|---|---|
| 3,478,600 | 11/1969 | Lynn | 73/432 |
| 3,561,253 | 2/1971 | Dorman | 73/28 |
| 3,564,264 | 2/1971 | Karuhn et al. | 250/218 |
| 3,595,078 | 7/1971 | Beck et al. | 73/194 F |
| 3,653,253 | 4/1972 | Olin | 73/28 |
| 3,678,759 | 7/1972 | Schneeberger | 73/432 PS |
| 3,731,464 | 5/1973 | Brumbaugh et al. | 55/270 |
| 3,739,180 | 6/1973 | Carlson | 250/218 |
| 3,763,428 | 10/1973 | Preist | 324/71 CP |
| 3,802,271 | 4/1974 | Bertelson | 73/432 PS |
| 3,805,591 | 4/1974 | Willis et al. | 73/28 |
| 3,844,174 | 10/1974 | Chabre | 73/432 PS |
| 3,854,321 | 12/1974 | Dahneke | 73/28 |
| 3,908,465 | 9/1975 | Bartlett | 73/432 PS |
| 3,938,366 | 2/1976 | Wertlake et al. | 73/28 |
| 4,007,969 | 2/1977 | Aubin et al. | 366/101 |
| 4,114,557 | 9/1978 | DeBrey | 116/67 R |
| 4,174,068 | 11/1979 | Rudolph | 222/630 |
| 4,189,937 | 2/1980 | Nelson | 73/28 |
| 4,212,190 | 7/1980 | Coover et al. | 73/28 |
| 4,274,846 | 6/1981 | Smith | 55/270 |
| 4,294,105 | 10/1981 | Kelly | 73/28 |
| 4,298,836 | 11/1981 | Groves et al. | 324/71 CP |
| 4,374,702 | 2/1983 | Turbak et al. | 241/28 X |
| 4,556,849 | 12/1985 | Kalakutsky | 324/464 |
| 4,573,801 | 3/1986 | Leschonski et al. | 222/630 |
| 4,610,395 | 9/1986 | Ford | 241/5 |
| 4,736,895 | 4/1988 | Hüttlin | 241/57 X |
| 4,860,959 | 8/1989 | Handleman | 241/5 |
| 4,895,034 | 1/1990 | Poole | 73/865.5 |
| 5,277,074 | 1/1994 | Poole | |
| 5,278,626 | 1/1994 | Poole et al. | 356/36 |
| 5,358,188 | 10/1994 | Makino et al. | 241/5 X |

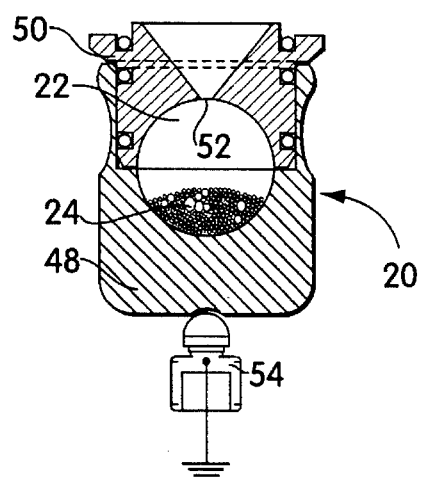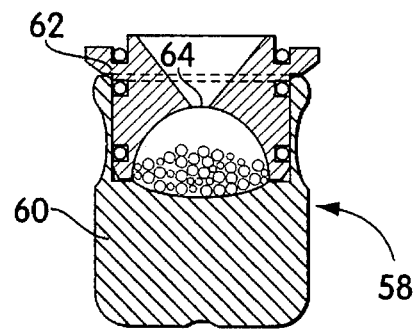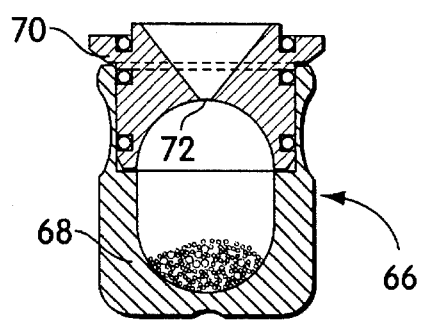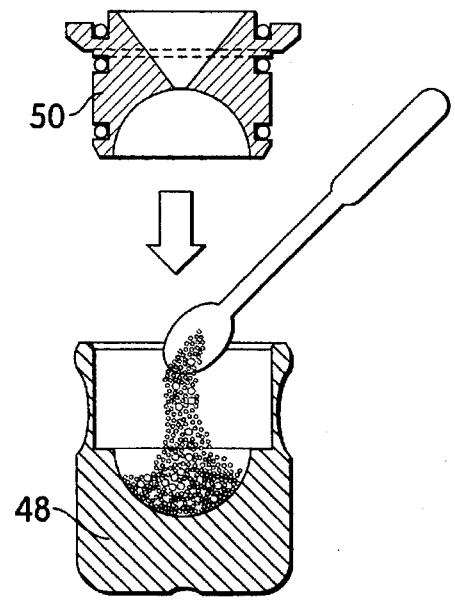
Fig. 2
Fig. 3
Fig. 4
Fig. 5

DRY POWDER DISPERSION SYSTEM

FIELD OF THE INVENTION

This invention relates to apparatus for dispersing dry particles in a gas stream for measurement and, more particularly, to apparatus for controlled dispersion of a powder sample into a gas stream. The powder dispersion system of the present invention is particularly useful for supplying particles to a particle sizing system utilizing a time-of-flight measurement technique, but is not limited to such use.

BACKGROUND OF THE INVENTION

Powders composed of coarse and fine particles are utilized in many industrial processes. Examples of powders include foods, pharmaceuticals, abrasives, pigments, plastics, magnetic coating materials and the like. The particles may range in diameter from less than one micrometer to one thousand micrometers. One known technique for particle size measurement utilizes a time-of-flight technique. An aerosol containing the particles to be measured is accelerated through a nozzle and is injected through two spaced-apart light beams in a vacuum chamber. As a particle passes through each light beam, light scattering occurs. A detector receives a scattered light pulse from the first beam and from the second beam for each particle. The time delay between pulses represents particle velocity, which is directly correlated to particle size. The output of such an instrument is typically a distribution of the number of particles measured at each particle size over a range of sizes. An example of such a system is the Aerosizer® particle sizing system manufactured and sold by Amherst Process Instruments, Inc.

A critical component of time-of-flight particle size measurement systems is the powder disperser which delivers a fully-suspended, evenly-dispersed, primary particle aerosol to the particle measurement zone. Samples of particles to be measured are often in the form of a dry powder sample. The powder sample is an agglomerated form of primary particles which are usually in clusters when in a cohesive state, as opposed to individual particles in a free flowing state. These clusters are due to several types of attraction mechanisms, working in part or together: electrostatic or Van Der Wall attraction, "thin film" liquid surface attraction, and mechanical surface geometry interlocking.

In order to accurately measure the particles using the time-of-flight technique, the clusters must be deagglomerated into individual particles and entrained into a gas stream for presentation to the measurement zone in a random, one at a time fashion. If agglomerated particles are not fully dispersed prior to entering the acceleration nozzle, they will be obliterated within the measurement zone. The result of this mal-dispersion condition is the rapid particulate coating of the source and detection optics. The fine powder build-up on these surfaces degrades instrument performance, thus demanding frequent optics cleaning and maintenance.

A powder disperser for an aerodynamic particle sizing system is disclosed in U.S. Pat. No. 4,895,034, issued Jan. 23, 1990 to Poole. The disclosed powder disperser directs a gas jet at a powder sample to produce a cloud of particles. The cloud of particles passes through an annular orifice. In the annular orifice, high shear forces are applied to the aerosol transport gas, which in turn places reaction forces upon the entrained particles.

Some particles are particularly resistant to dispersion in a gas stream. These powders, known as highly cohesive powders, are typically composed of very small particles. Examples of highly cohesive powders include $TiO_2$, $CrO_2$, magnetic powders, polymer toners and micronized pharmaceuticals. Typically, such powders have been analyzed by suspending the powder in a liquid, called a wet dispersion process. This approach requires finding a compatible solvent and requires extra care in the disposal of contaminated solvents. Furthermore, liquids cannot be used in a time-of-flight particle size measurement system, except in the form of droplets which carry selective particle sizes.

It is desirable to provide a powder disperser which is capable of handling highly cohesive powder samples. In particular, the powder disperser should deagglomerate the powder sample into its constituent particles and supply the particles at a controlled rate. The tendency for particles to stick to surfaces in the powder disperser should be minimized.

SUMMARY OF THE INVENTION

In accordance with a first aspect of the invention, apparatus for dispersion of particles in a gas comprises a structure defining a rapid acceleration chamber, a momentum tube for supplying particles to the rapid acceleration chamber and an annular nozzle at an outlet of the rapid acceleration chamber for dynamic shear dispersion of the particles. The rapid acceleration chamber contains an impact surface for impingement and deagglomeration of particles that are received through the momentum tube. The apparatus further includes means for supplying a gas stream through the rapid acceleration chamber between the impact surface and the annular nozzle, and means for mechanically dithering the annular nozzle such that the annular nozzle tends to remain free from particle buildup. The structure defining the rapid acceleration chamber and the annular nozzle preferably comprises a housing and a disperser pin mounted within the housing. The disperser pin is translated along its longitudinal axis relative to the housing to maintain the annular nozzle free from particle buildup.

Preferably, the impact surface is formed on the disperser pin. In one embodiment, the impact surface and the momentum tube are configured such that the particles received from the momentum tube impinge on the impact surface at a tangential grazing angle. In another embodiment, the disperser pin is rotated relative to the momentum tube. In each case, perpendicular impingement of particles on the impact surface is avoided to the extent possible.

The gas stream preferably comprises an annular gas curtain through the rapid acceleration chamber, and a transport gas stream. The transport gas stream passes through the momentum tube and combines with the annular gas curtain in the rapid acceleration chamber. Particles pass through the annular gas curtain before impingement on the impact surface. The velocity of the transport gas through the momentum tube can be controlled to thereby control the momentum of agglomerates that impinge on the impact surface.

The rapid acceleration chamber has a rapidly converging hog horn shape which rapidly accelerates the gas stream between the impact surface and the annular nozzle. Residual agglomerates are subjected to dynamic shear, gas reaction forces in the annular nozzle. The annular nozzle preferably has an annular gap defined between a sharp ridge on the disperser pin and a truncated conical inside surface of the housing. As the disperser pin is translated along its longitudinal axis, the width of the annular gap is varied.

According to another aspect of the invention, the apparatus may include a fluidization assembly for fluidizing a powder sample into particles and for entraining the particles in a transport gas stream flowing through the momentum tube. The fluidization assembly comprises a primary chamber for holding the powder sample, and a secondary chamber for mixing particles of the powder sample with the transport gas stream. The secondary chamber is located above the primary chamber. The primary and secondary chambers are connected by an opening at the upper end of the primary chamber. The momentum tube is connected to the secondary chamber. The fluidization assembly further includes means for directing a pulsed gas jet through the opening into the primary chamber for dispersing the particles of the powder sample into the secondary chamber, and means for directing the transport gas stream through the secondary chamber for transporting the particles from the secondary chamber through the momentum tube.

The upper and lower ends of the primary chamber are preferably substantially hemispherical in shape. The depth of the primary chamber is decreased for powder samples with large particles and/or high mass density and is increased for powder samples with small particles and/or low mass density. The secondary chamber preferably has a conical lower end centered on the opening to the primary chamber so that particles not transported through the momentum tube fall back through the opening into the primary chamber.

The gas pulses directed into the primary chamber are successively increased in pressure until a desired pressure is reached. The transport gas stream enters the secondary chamber in an annular flow pattern, thereby causing a toroidal vortex swirl within the secondary chamber for entraining the particles in the transport gas stream.

A removable sample cup defines the primary chamber. The sample cup includes a base for receiving the powder sample and a cap having an opening to the secondary chamber. The sample cup is preferably electrically grounded so as to reduce static charge on the powder sample.

According to a further aspect of the invention, apparatus for dispersion of particles in a gas comprises a dynamic shear dispersion nozzle, a first conduit located upstream of the dynamic shear dispersion nozzle, the first conduit having an inlet for receiving particles, a second conduit located downstream of the dynamic shear dispersion nozzle, means for supplying a transport gas stream through the first conduit and the dynamic shear dispersion nozzle to the second conduit for transporting the particles through the dynamic shear dispersion nozzle, and feedback means for dynamically controlling the dynamic shear force on the transport gas stream, which in turn places reaction forces upon the particles, within the dynamic shear dispersion nozzle.

Preferably, the dynamic shear dispersion nozzle includes an annular gap for the dynamic shear dispersion effect on the particles. The feedback means comprises gap control means for dynamically controlling width of the annular gap. In a preferred embodiment, the gap control means comprises means for sensing the differential pressure across the dynamic shear dispersion nozzle, means responsive to the difference between the sensed differential pressure and a desired value of the differential pressure for determining an error in the differential pressure, and means responsive to the error for varying the annular gap so as to reduce the error. The annular gap is preferably varied by displacing the disperser pin relative to the housing.

BRIEF DESCRIPTION OF THE DRAWINGS

For a better understanding of the present invention, reference is made to the accompanying drawings which are incorporated herein by reference and in which:

FIGS. 2–4 show different sample cup configurations that can be utilized in the powder disperser of FIG. 1B;

FIG. 5 illustrates the placement of a powder sample in the sample cup;

DETAILED DESCRIPTION

Figure 1A:
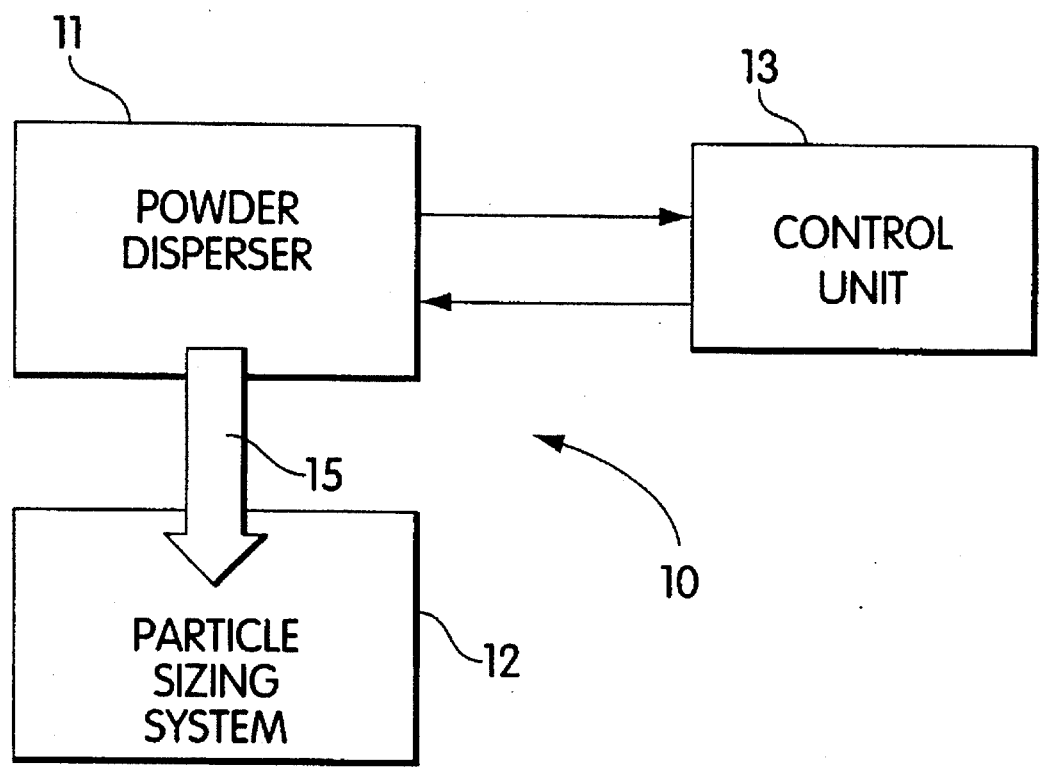
FIG. 1A is a schematic block diagram that shows the powder dispersion system of the present invention.
Figure 1B:
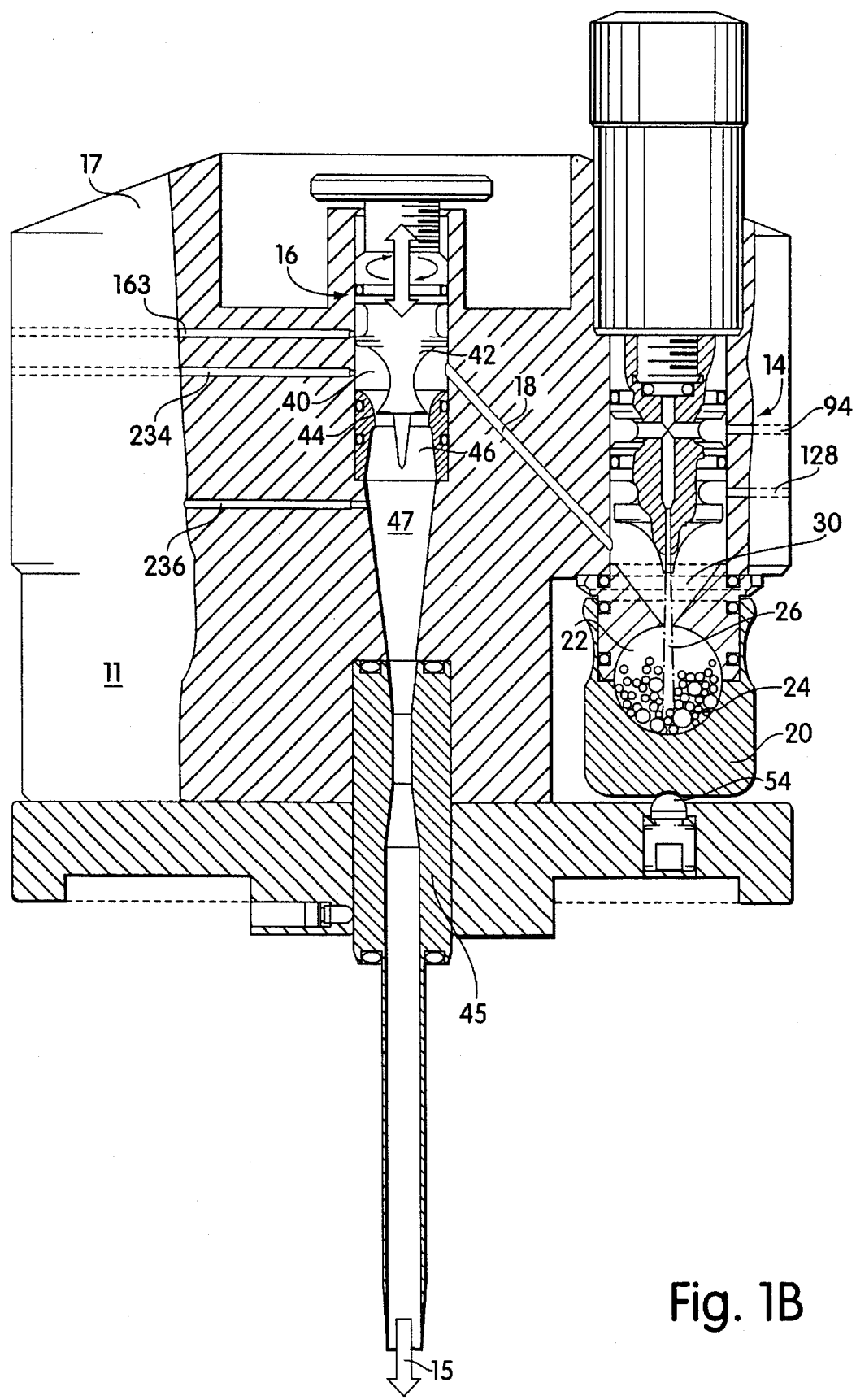
FIG. 1B is a schematic elevation view of the powder disperser of FIG. 1A.

A powder dispersion system 10 in accordance with the present invention is shown in FIGS. 1A and 1B. The powder dispersion system 10 supplies a particle stream 15 at a controlled rate to a particle sizing system 12 for measurement of the particles and/or a particle composition spectrometer analyzer (not shown). The particle sizing system can, for example, be an Aerosizer time-of-flight particle measurement system manufactured and sold by Amherst Process Instruments, Inc. Particle sizing system 12 measures the particle sizes and typically produces a plot of the distribution of particle sizes in a powder sample. It will be understood that the powder dispersion system can be used to supply a stream of particles to any desired instrument, process device or other equipment.

The powder dispersion system 10 includes two major components: a powder disperser 11 and a control unit 13. The powder disperser 11, shown in FIG. 1B, includes a fluidization assembly 14 and a dynamic shear dispersion assembly 16 interconnected by a momentum tube 18. The fluidization assembly 14 and the dynamic shear dispersion assembly 16 are mounted in a housing 17. The fluidization assembly 14 includes a sample cup 20 that defines a primary chamber 22 for placement of a powder sample 24. A pulsed gas jet 26 directed into the primary chamber 22 causes primary deagglomeration and dispersion of the powder sample 24 in the primary chamber 22. The pulsed gas jet 26 disperses particles of the powder sample 24 into a secondary chamber 30 located above primary chamber 22. A transport gas stream directed through secondary chamber 30 entrains particles of the powder sample and carries the particles through the momentum tube 18 as an aerosol to the dynamic shear dispersion assembly 16. The particles transported through momentum tube 18 enter a rapid acceleration chamber 40 and impinge upon an impact surface 42. The particles are further deagglomerated upon impingement on impact surface 42 and then are accelerated through the rapid acceleration chamber 40 to an annular nozzle 44, where the particles are further broken apart by dynamic shear dispersion. After passing through the annular nozzle 44, the aerosol is expanded into a diverging tube 46 followed by a converging tube 47. The particle stream is then directed through a tuned transport tube 45 into the particle sizing system 12 for measurement.

The housing 17 of the powder disperser 11 is preferably fabricated of a transparent acrylic. The housing has two important features: (1) the transparent material permits visual inspection of the gas conduits for excessive deposition and contamination, which indicates that cleaning is required and (2) the acrylic material serves as an insulator to maintain the gas conduits and component parts at a constant temperature, with minimal heat transfer to the ambient environment. This is due to the relatively high specific heat of plastics and their poor conductance characteristics. By maintaining the conduits and component parts at a temperature higher than the ambient, the powder disperser does not suffer from condensation of the water vapor in the transport gas. The elevated transport gas temperature is produced by the compressor pumps at the front end of the pneumatic support system.

The sample cup 20 serves three purposes: (1) as a container to hold the powder sample 24, (2) as a controlled fluidization chamber where initial particle deagglomeration and aerosol cloud formation occurs, and (3) as an electrostatic ground for reduction of particle charge. As shown in FIG. 2, the sample cup 20 includes a base 48 and a sealed interlocking cap 50. The base 48 and the cap 50 define the primary chamber 22 where the powder sample 24 is placed and where initial processing of the powder sample takes place. The cap 50 has an on-center exit hole 52 which allows the particles of the powder sample to escape from the primary chamber 22. A grounded electrostatic discharge contact 54 contacts the conductive base 48 of sample cup 20 and minimizes electrostatic charge on the particles of the powder sample 24.

Two critical dimensions of the sample cup are the depth of the primary chamber 22 and the diameter of exit hole 52. In order to accommodate a wide range of powder types and particle sizes, several sample cup configurations are utilized as shown in FIGS. 2–4. In FIG. 2, the base 48 has a medium depth and the cap 50 has a medium diameter exit hole 52. FIG. 3 illustrates a sample cup 58 with a shallow base 60 and a cap 62 with a large diameter exit hole 64. FIG. 4 illustrates a sample cup 66 with a deep base 68 and a cap 70 with a small exit hole 72. In general, the base depth should become greater as the mass density of the powder sample becomes smaller. This inverse relationship is due to the pneumatic uplift mechanics of the powder entrainment process. The heavier the powder sample, the more pneumatic energy required. Therefore, large and/or heavy particles should be sampled in a shallow base, and small and/or light particles should be sampled in a deep base. The interchangeable two component base/cap configuration allows the primary chamber of the sample cup to be arranged in a matrix of possible geometries. Three caps and three bases provide nine possible primary chamber geometries. This extended geometry capability provides greater powder morphology handling capability, and is useful when the samples are inversely related, such as large particles that are light in weight or small particles that are heavy in weight.

The shape of the primary chamber 22 is also important to achieve efficient fluidization. In the sample cup 20 with a medium depth base 48, the primary chamber 22 is approximately spherical. In sample cup 58 with a shallow base 60, the radius of the lower portion of the primary chamber is increased in comparison with FIG. 2 so as to reduce the primary chamber depth. In the sample cup 66 with a deep base 68, the spherical shape of FIG. 2 is elongated to produce a primary chamber with a generally oval cross-section. The upper and lower ends of the primary chamber in sample cup 66 are hemispherical. In each case, the cavities in the cap and the base which define the primary chamber should have smoothly curved surfaces, so as to avoid locations where particles can build up.

The diameter of exit hole 52 in cap 50 is determined by the particle size and density of the powder sample 24. The exit hole is typically large enough to pass the largest anticipated sample particle, with a four times clearance margin. For example, a 700 µm particle typically requires a 3 mm diameter exit hole. The small exit hole restricts the aerosol contents within the primary chamber 22 from being prematurely induced into the transport gas stream until the pulsed gas jet is activated. By way of example, the small exit hole 72 can be 1.5 mm, the medium exit hole 52 can be 2.5 mm and the large exit hole 64 can be 3.0 mm.

Figure 6:
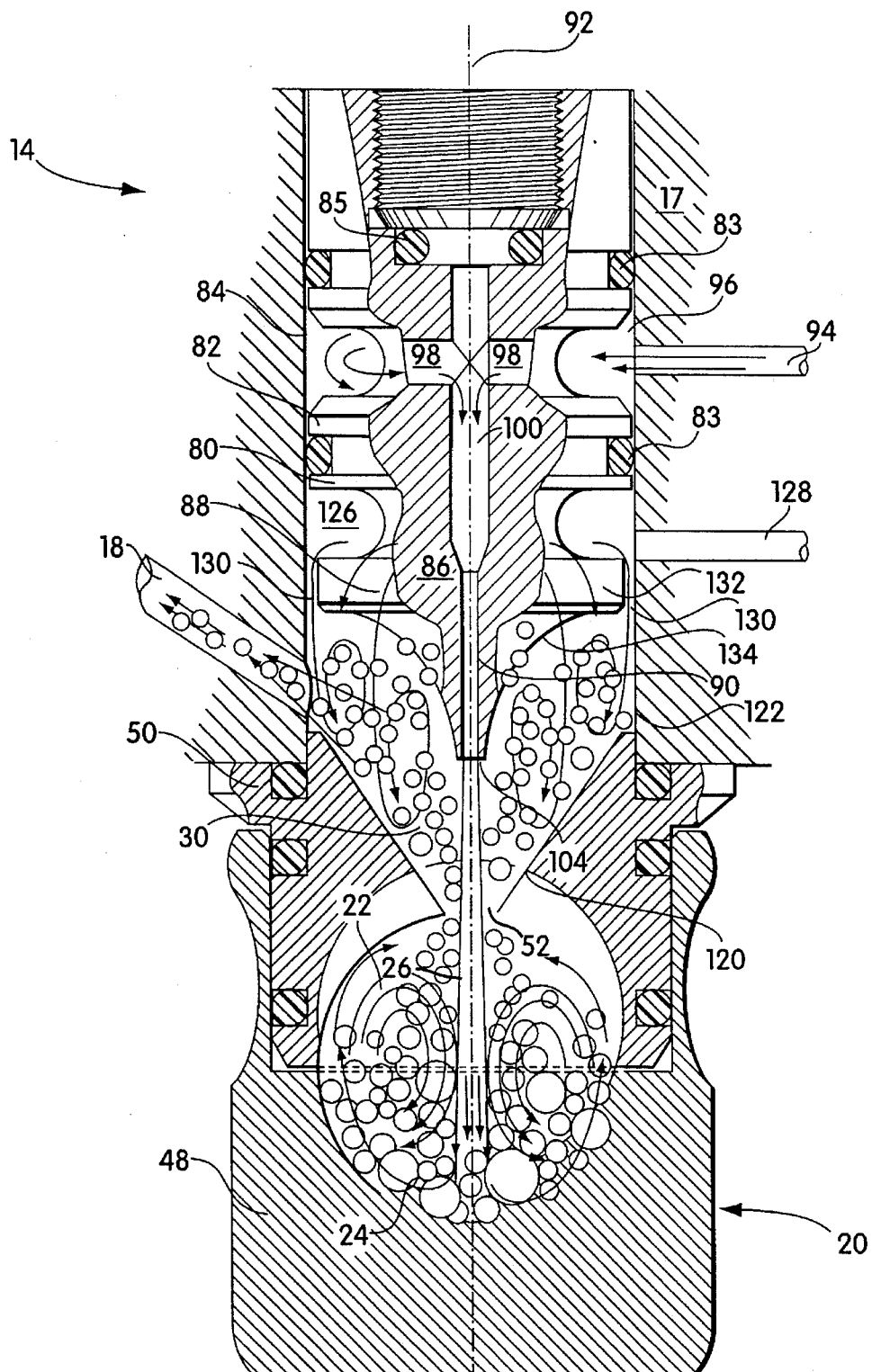
FIG. 6 is an enlarged, cross-sectional view of the fluidization assembly.

An enlarged cross-sectional view of the fluidization assembly 14 is shown in FIG. 6. The powder sample 24 in primary chamber 22 is fed into a continuously flowing transport gas stream by the pulsed gas jet 26. This highly collimated, tightly controlled gas jet passes through exit hole 52 of primary chamber 22 and impinges directly on the powder sample 24 at the bottom of the sample cup 20. The gas jet is pulsed to provide a modulated burst of gas. Through gas modulation, the force and duration of the gas jet upon the powder sample can be precisely controlled, thereby permitting accurate management of the powder sample fluidization, initial deagglomeration and the steady state dispersion of particles into an aerosol cloud within the primary chamber 22.

The gas jet 26 is directed from a gas manifold assembly 80 into the primary chamber 22. The gas manifold assembly 80 includes a gas manifold element 82 sealed into a cylindrical bore 84 in housing 17 by O-ring seals 83 and 85. The gas manifold assembly 80 has two primary functions: (1) to direct the pulsed gas jet 26 through a gas jet nozzle 86 into primary chamber 22 and (2) to direct an annular gas stream 88 into secondary chamber 30. The pulsed gas jet 26 is supplied through a conduit 90 in gas jet nozzle 86. The conduit 90 is located on a central longitudinal axis 92 of the fluidization assembly 14. Pulsed gas is supplied through a conduit 94 in housing 17 to an annular conduit 96 defined by an annular groove in gas manifold element 82. The pulsed gas is conducted from annular conduit 96 through radial conduits 98 and axial conduit 100 formed in gas manifold element 82 to conduit 90.

The conduit 90 preferably has a length of 125 D, where D is the diameter of orifice 104 of the gas jet nozzle 86. A smaller nozzle orifice, preferably 0.030 inch, provides a higher impingement force per unit strike area, at a lower pulse gas volume flow rate. The smaller orifice can be used for highly agglomerated samples. A larger nozzle orifice, preferably 0.040 inch, provides a lower impingement force per unit strike area at a higher pulse gas volume flow rate. The larger orifice can be used for highly charged fine particles.

Figure 7:
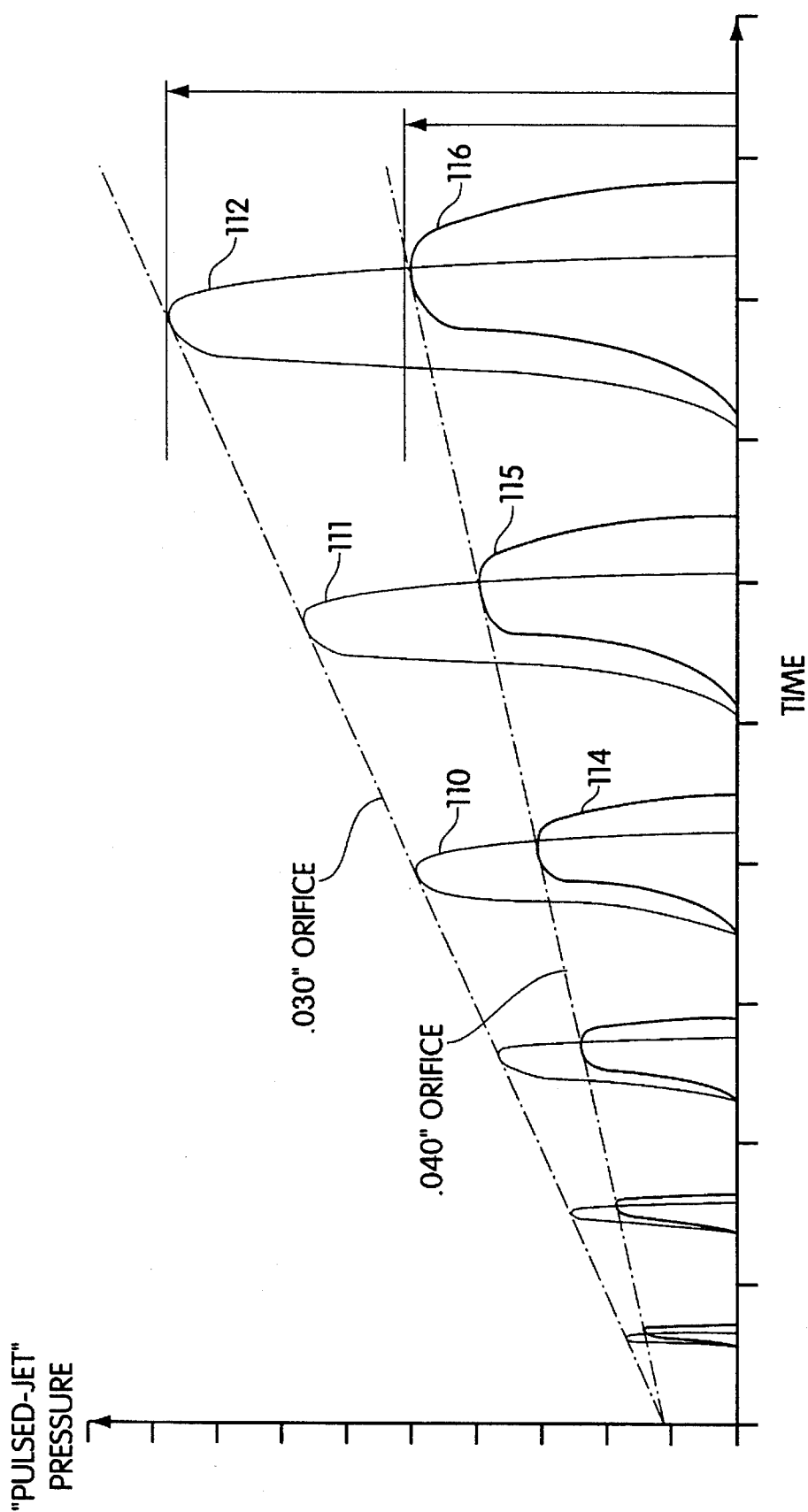
FIG. 7 is a graph of pulse jet pressure as a function of time for two different pulse jet orifice dimensions.

The pulsed gas jet 26 is preferably ramped from an initial low value to a steady state value as shown in FIG. 7. Pulsed jet pressure is plotted as a function of time in FIG. 7. Pulses 110, 111, 112, etc. represent the ramped gas jet pressure for a relatively small diameter orifice in gas jet nozzle 86. Pulses 114, 115, 116, etc. represent the ramped gas jet pressure for a relatively large diameter orifice in gas jet nozzle 86. Control of the pulsed gas jet 26 is described in detail below in connection with FIG. 11.

The pulsed gas jet 26 pressurizes the primary chamber 22 and initiates the powder sample breakdown, fluidization and entrainment processes. The pulsed gas jet, directed into the primary chamber, performs three functions to prepare different sample morphologies for particle measurement and analysis: (1) particle breakdown through collision mechanics, (2) gas jet impingement particle deagglomeration/fluidization, and (3) fine particle surface scavenging entrainment. In the collision mechanism, swirling aggregate particles break up into subparticles through interparticle and chamber wall surface collisions. Typical applications are chromium oxide powder and titanium dioxide powder. In the impingement deagglomeration mechanism, fluidized agglomerates are sheared into subclumps by direct gas beam impingement when passing through the target zone of the gas jet 26. Typical applications include process food powders and pharmaceutical powders. In the surface scavenging mechanism, charged fine particles cling to the wall of primary chamber 22 and creep along the surface until broken loose by grazing, scavenging gas flow or vortex shedding gas at the exit orifice. Typical applications include printer toners, paint pigments, magnetic powders, charged polymer powders and freeze-dried powders.

With reference to FIG. 6, the secondary chamber 30 has a bottom wall 120 defined by cap 50 and a cylindrical sidewall 122 defined by the bore 84 in housing 17. The top of secondary chamber 30 is defined by gas jet nozzle 86. Momentum tube 18 enters secondary chamber 30 through cylindrical sidewall 122. The gas manifold assembly 80 includes an annular manifold 126, defined by an annular groove in manifold element 82, that receives gas through conduit 128 in housing 17. A transport gas stream 88 is directed from annular manifold 126 through an annular gap 130 between housing 17 and a circular ridge 132 on gas manifold element 82 into secondary chamber 30.

The annular transport gas stream 88 creates a toroidal vortex swirl within the secondary chamber 30. The swirl allows the particle laden gas from the primary chamber 22 to emerge into the toroidal vortex of the secondary chamber 30. This action promotes particle entrainment and mixing conditions over a large gas pickup area at low particle concentration levels to reduce the occurrence of particle stackup reagglomeration. Particles of the powder sample in the secondary chamber 30 are in the process of becoming fully suspended within the transport gas stream, and first level entrainment/deagglomeration is complete. Large agglomerate clumps that cannot be suspended in the transport gas stream, because the gas stream velocity is not sufficient to entrain the agglomerate body, will fall back into the primary chamber 22 through exit hole 52 for further size reduction until they reach a transportable size.

Preferably, the bottom wall 120 of secondary chamber 30 has a truncated conical shape centered on exit hole 52. This permits large agglomerates in secondary chamber 30 to fall back through exit hole 52 into primary chamber 22. The orifice 104 of gas jet nozzle 86 is centered on exit hole 52 and on axis 92. An outer surface 134 of gas jet nozzle 86 has a concave curvature, as shown in FIG. 6, and forms a surface of revolution about axis 92. The contour of outer surface 134 promotes the toroidal vortex swirl within secondary chamber 30. The transport gas stream 88 exits from secondary chamber 30 through momentum tube 18 with entrained particles of the powder sample.

Figure 8:
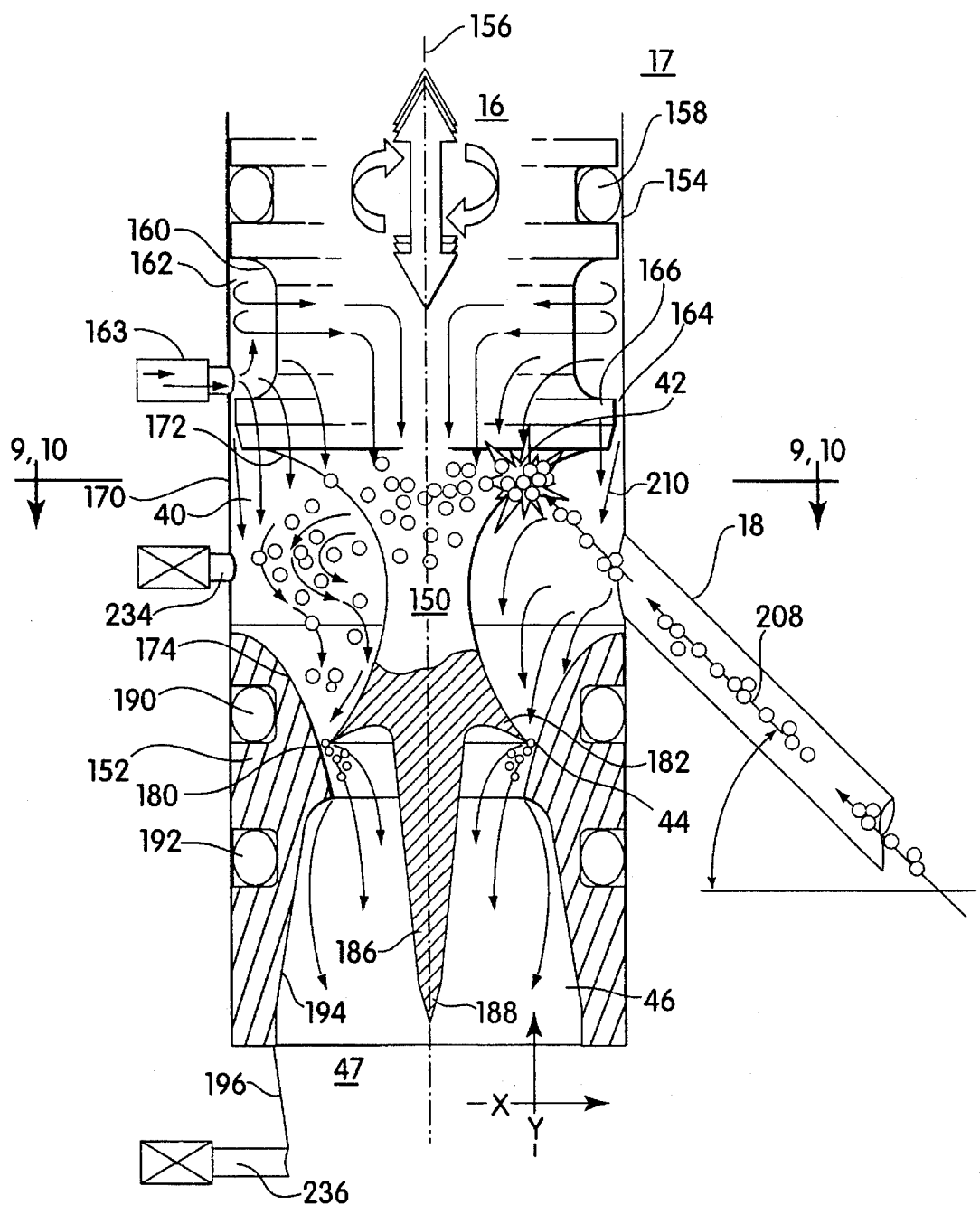
FIG. 8 is an enlarged, cross-sectional view of the dynamic shear dispersion assembly.

The momentum tube 18 links the secondary chamber 30 to the rapid acceleration chamber 40 (see FIGS. 1 and 8). Through gas to particle momentum transfer mechanics, the entrained particles are accelerated to the transport gas speed within the momentum tube 18. With reference to FIG. 8, the particles passing through momentum tube 18 enter the rapid acceleration chamber 40 and impinge upon the impact surface 42 for further powder sample agglomerate reduction. By this controlled impaction method, the transport gas velocity in the momentum tube 18 can be adjusted to produce any appropriate impingement force. The transport gas stream through the momentum tube 18 can be adjusted to different preset levels. The particles within the gas stream reach the terminal velocity of the gas stream. This, in turn, causes the particles to impinge on the impact surface 42 at different preset levels of momentum force. The momentum force of impingement is determined by the mass of the suspended particles multiplied by the velocity of the transport gas stream. The transport gas velocity is controlled by diverting a part of the transport gas from the secondary chamber 30 to the rapid acceleration chamber 40 through a bypass conduit. The gas stream through the momentum tube 18 and the gas diverted through the bypass conduit are recombined in the rapid acceleration chamber 40 to achieve a constant flow rate to the particle sizing system. The above-described impingement force and velocity control permit the apparatus to be adjusted to maintain optimum deagglomeration force within the fragility limits of the sample. For example, too much impact on a high aspect ratio or fragile powder sample may fracture the primary particles of the sample and create fines, as well as undersized primary particles.

The momentum tube 18 is designed for velocity control of the transport gas stream and is configured at an optimum updraft angle of approximately 45° with respect to a longitudinal axis 156 of the dynamic shear dispersion assembly 16. With this updraft angle, the momentum tube 18 intersects the secondary chamber 30 and the rapid acceleration chamber 40 at an optimum hydraulic angle. The 45° intersection produces a more efficient conduit suction/discharge port by enhancing the hydraulic radius and edge effect of the momentum tube 18. Inefficient tube end geometries perturb the gas flow and tend to promote gas rotation factors which enhance particle collision as well as reagglomeration. An enlarged, cross-sectional view of the dynamic shear dispersion assembly 16 is shown in FIG. 8. The principle structural components of the dynamic shear dispersion assembly 16 are the housing 17, a movable disperser pin 150 and a disperser bowl 152. The housing 17 is provided with a cylindrical bore 154 in which the disperser pin 150 and the disperser bowl 152 are mounted. The convergence tube 47 is formed in housing 17 at the lower end of cylindrical bore 154 and is coaxial with cylindrical bore 154.

The disperser pin 150 is symmetrical about the longitudinal axis 156 and is sealed into the cylindrical bore 154 by a sliding O-ring seal 158. An annular groove 160 in disperser pin 150 defines an annular manifold 162. Gas is supplied to the annular manifold 162 through a conduit 163 in housing 17. An annular gap 164 is defined between housing 17 and a circular rib 166 on disperser pin 150. As discussed below, annular gap 164 permits an annular gas curtain to flow from annular manifold 162 to rapid acceleration chamber 40.

The rapid acceleration chamber 40 has a converging "hog-horn" shape which channels the particle-laden aerosol from the impact surface 42 to the dynamic shear dispersion region in annular nozzle 44 in a rapid, yet smooth accelerating flow, with minimal dead zones which encourage particle deposition and particle reagglomeration. The rapid acceleration chamber 40 is defined by a cylindrical wall 170 of housing 17, a curved surface 172 of disperser pin 150 and an inside surface 174 of disperser bowl 152. In a plane containing longitudinal axis 156, as shown in FIG. 8, the curved surface 172 has a continuous concave curvature between impact surface 42 and annular nozzle 44. The impact surface 42 is an area on curved surface 172 where the particle stream from momentum tube 18 impinges. The inside surface 174 of disperser bowl 152 is curved in an upper portion adjacent to sidewall 170 and is linear in a region adjacent to annular nozzle 44. The curved surface 172 of disperser pin 150 and the inside surface 174 of disperser bowl 152 are surfaces of revolution about longitudinal axis 156. Thus, inside surface 174 has a truncated conical shape adjacent to annular nozzle 44. In general, the rapid acceleration chamber 40 has a shape that converges rapidly toward annular nozzle 44.

The annular nozzle 44 comprises an annular gap 180 between the inside surface 174 of disperser bowl 152 and a sharp annular ridge 182 on disperser pin 150. Since the inside surface 174 has a truncated conical shape, the width of annular gap 180 is a linear function of the displacement of disperser pin 150 along longitudinal axis 156. Curved surface 172 extends between circular rib 166 and sharp annular ridge 182. The disperser pin 150 has a circular cross-section in this region.

The disperser pin 150 further includes a tapered portion 186 that extends from annular nozzle 44 into divergence tube 46. In a preferred embodiment, the tapered portion 186 has a double taper: a primary taper at an angle of 5.5° full angle and a tip 188 with a taper at an angle of 30° full angle. This configuration promotes a smooth gas flow with reduced eddies in divergence tube 46 and limits particle sticking to tapered portion 186.

The disperser bowl 152 is sealed within the cylindrical bore 154 of housing 17 by O-ring seals 190 and 192. As described above, the inside surface 174 of disperser bowl 152 defines a portion of the rapid acceleration chamber 40 and the annular gap 180 of annular nozzle 44. The disperser bowl 152 also defines the divergence tube 46. Preferably, a wall 194 of divergence tube 46 diverges from longitudinal axis 156 at an angle of about 20° full angle. A wall 196 of convergence tube 47 converges toward longitudinal axis 156 at a preferred angle of about 20° full angle (or 10° half angle).

Figure 11:
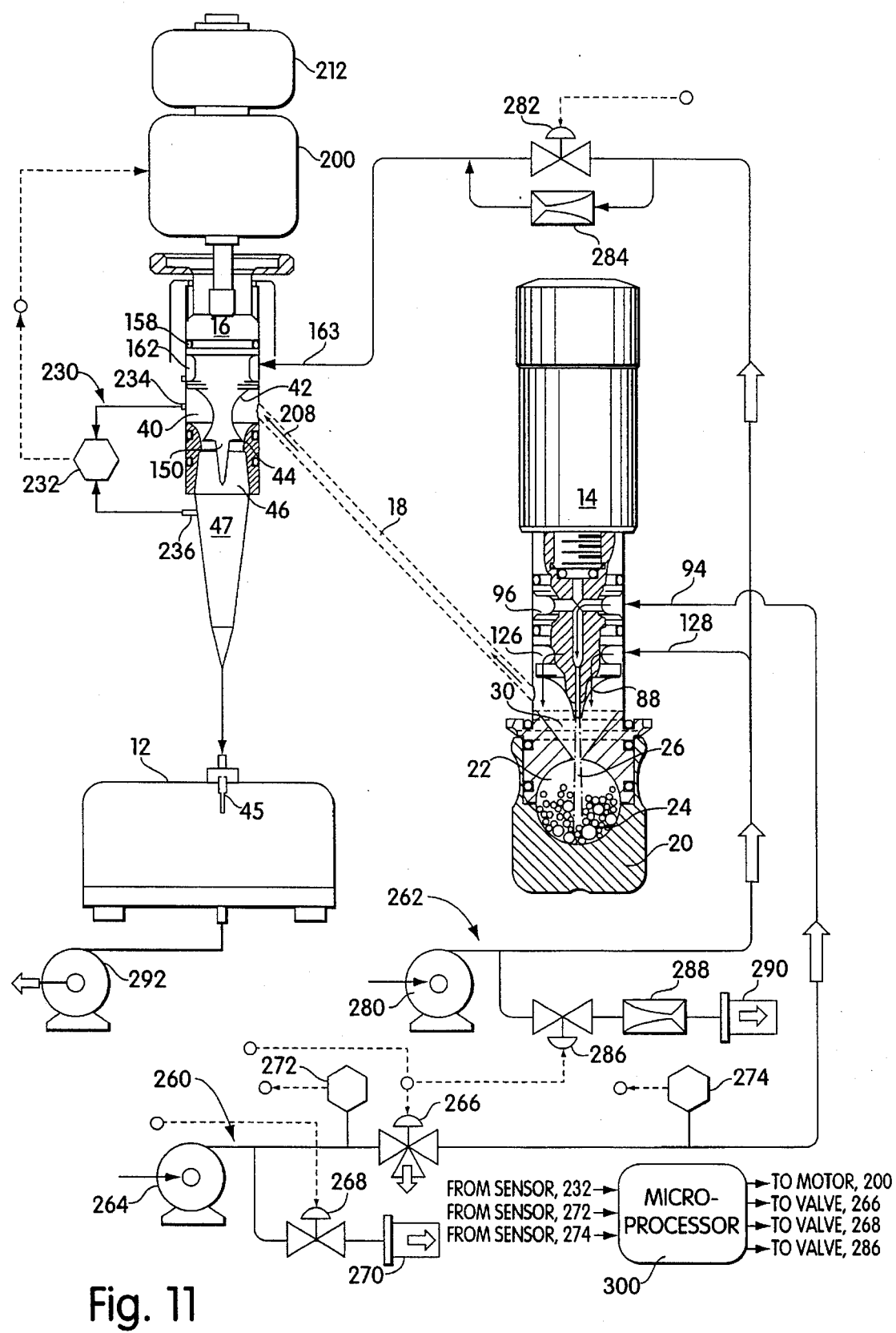
FIG. 11 is a schematic diagram that illustrates the control unit of the powder dispersion system.

The disperser pin 150 is connected to a stepper motor 200 (shown in FIG. 11). The stepper motor 200 permits controlled linear movement of the disperser pin 150 along longitudinal axis 156, as described below. In particular, the stepper motor 200 permits the width of the annular gap 180 to be adjusted to a desired value and permits feedback control of the annular gap 180. In addition, the stepper motor 200 permits the disperser pin 150 to be dithered, or oscillated, with a small displacement along longitudinal axis 156 to prevent particle buildup in the annular gap 180.

The transport gas that carries particles through the rapid acceleration chamber 40 to the annular nozzle 44 comes from two sources. A first portion of the transport gas passes through the momentum tube 18 as transport gas stream 208 and carries particles from the secondary chamber 30 to the rapid acceleration chamber 40. A second portion of the transport gas is supplied to rapid acceleration chamber 40 through annular gap 164 as an annular gas curtain 210. Gas from the two sources combines in the rapid acceleration chamber 40 and carries the particles through annular nozzle 44, divergence tube 46 and convergence tube 47 by way of the tuned transport tube 45, then to the particle sizing system 12. As noted above, the relative proportions of the transport gas stream 208 and the annular gas curtain 210 may be adjusted so as to control the velocity of the transport gas stream 208 in momentum tube 18. However, the total gas flow rate through annular nozzle 44 is more or less constant.

Figures 9, 10:
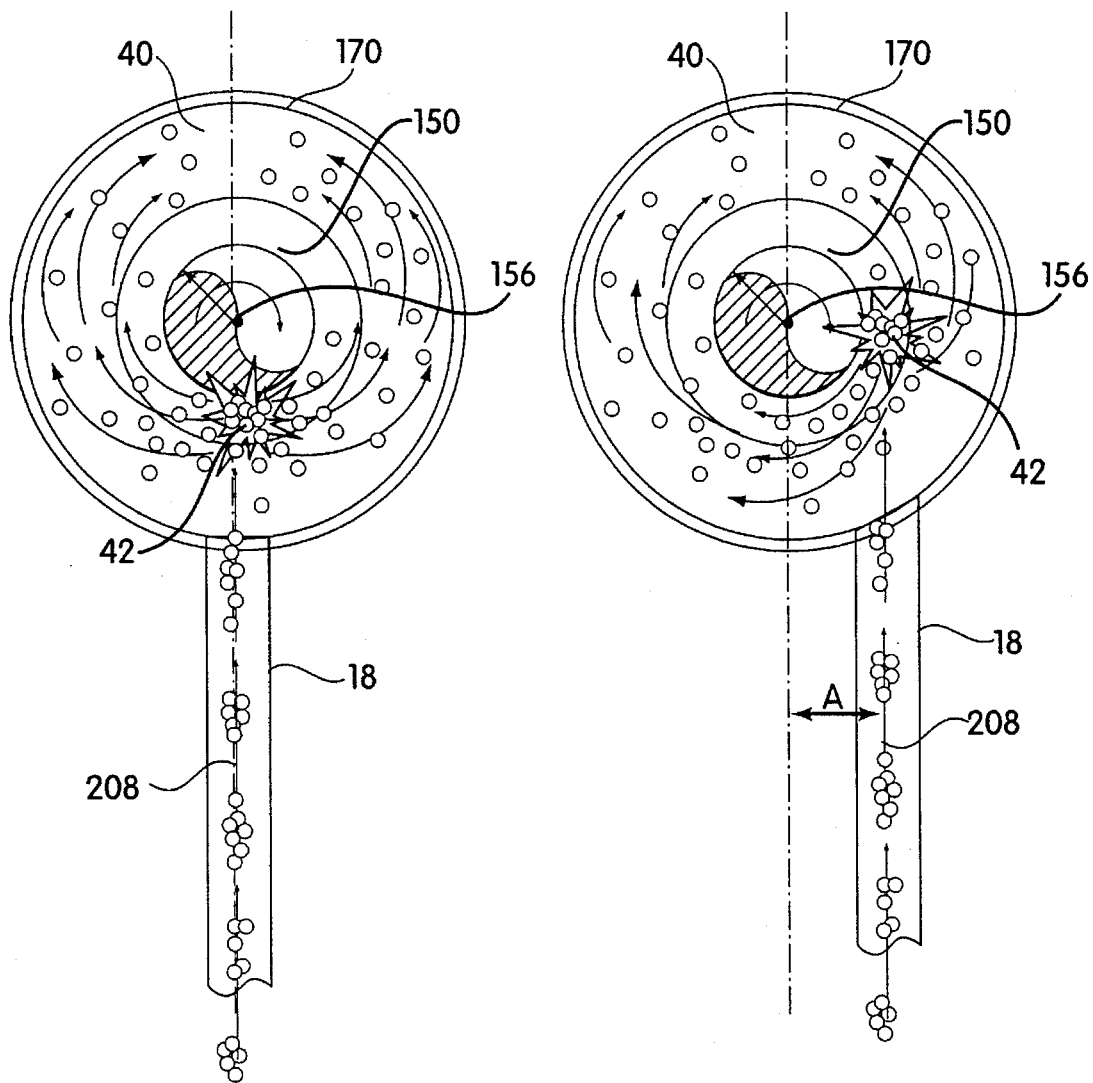
FIG. 9 is a cross-sectional view of the rapid acceleration chamber, illustrating impingement of particles on the impact surface at a tangential grazing angle.
FIG. 10 is a cross-sectional view of the rapid acceleration chamber, illustrating impingement of particles on a spinning impact surface.

The impact surface 42 is an important component of the powder disperser. Particles passing through momentum tube 18 impinge on impact surface 42 and undergo further deagglomeration and particle separation. An important feature of the impact surface 42 is that it is configured to avoid, to the extent practical, perpendicular impingement of the particle stream. Such perpendicular impingement is likely to cause reagglomeration of particles, because the particles rebound from the surface along the incoming path and tend to reagglomerate with incoming particles. As shown in FIG. 8, impact surface 42 has a continuous concave curvature in a plane containing longitudinal axis 156. As shown in FIGS. 9 and 10, the impact surface 42 has a continuous convex curvature in a plane perpendicular to longitudinal axis 156. The curved contour of the impact surface 42 tends to reduce perpendicular impingement of particles.

In one embodiment of the dynamic shear dispersion assembly 16, shown in FIG. 9, the momentum tube 18 is offset from the longitudinal axis 156 of disperser pin 150, so that particles passing through momentum tube 18 are incident upon impact surface 42 at a tangential grazing angle. The momentum tube 18 is preferably offset from the longitudinal axis 156 by a distance A on the order of 4–5 mm, and the particles are preferably incident on impact surface 42 at an angle of about 37°–50°.

In a second embodiment of the dynamic shear dispersion assembly 16, shown in FIG. 10, the disperser pin 150 is rotated at high speed about longitudinal axis 156 by a suitable rotation motor 212 (FIG. 11). In this embodiment, momentum tube 18 can be aligned with longitudinal axis 156 as shown in FIG. 10, or can be offset from longitudinal axis 156, as shown in FIG. 9. The particles impinge on a rapidly spinning impact surface 42. The rotation of the impact surface 42 causes impinging particles to be deflected in the direction of rotation and to be deagglomerated upon impact. As a result, particles are effectively dispersed in the rapid acceleration chamber 40. The disperser pin 150 can be rotated in either direction. As indicated above, the sample powder aerosol passes from the momentum tube 18 into the rapid acceleration chamber 40 and impinges directly on the impact surface 42 of disperser pin 150. Prior to impinging on the impact surface 42, the particles pass through a small portion of the annular gas curtain 210. The gas curtain emerges from the annular gap 164 between housing 17 and circular rib 166 of disperser pin 150. Controlled secondary deagglomeration of the powder sample takes place within the downdraft/crossflow environment of the annular gas curtain 210. The impact surface 42 on the disperser pin is contoured into a reverse curving geometry as described above. The impact surface 42 serves two vital functions: (1) to redirect the transport gas stream 208 emerging from the momentum tube 18 without major flow maldistribution, and (2) to establish a grazing angle surface for impingement of the multi-sized sample powder agglomerates. The disperser pin geometry forms a three-dimensional impact surface at the intersection of two orthogonal radii. The impingement of particles at a grazing angle or on a spinning surface is critical in achieving the optimum breakup of agglomerates with minimum bounce-back and maximum particle separation without primary particle fracture. This configuration reduces particle bounce-back and reagglomeration, and also reduces particle buildup on the impact surface.

The annular gas curtain 210 has three important functions: (1) to create a curtain of sheath gas which entrains and directs most of the residual agglomerate particles to the dynamic shear dispersion region in annular nozzle 44, (2) to prevent particles from contaminating the dynamic O-ring seal 158 of disperser pin 150 and the surface upon which the O-ring seal 158 slides, and (3) the annular gas curtain 210 provides a bypass path for transport gas as the velocity of the transport gas stream through momentum tube 18 is varied. The transport gas diverted from the momentum tube 18 is introduced into the rapid acceleration chamber 40 as the annular gas curtain 210 so that the overall gas flow rate to the particle sizing system 12 remains constant.

The powder sample aerosol is rapidly accelerated from the impact surface 42 through the convergent shape of the rapid acceleration chamber 40 and is extruded through the annular nozzle 44. The aerosol is then expanded into diverging tube 46. The expanding gas discharge from the annular nozzle 44 operates primarily within, but is not limited to operation within, the subsonic to transonic gas flow regime. The expanding gas plume transfers its high pneumatic energy to the particle phase of the aerosol by a gas kinetic process. This process provides the final deagglomeration and the complete particle aeration of the powder sample.

The annular gap 180 is set to a gap width that will pass the largest primary particle of the powder sample. The residual agglomerates that are larger than the width of annular gap 180 become lodged directly above the gap. The local differential pressure between the upstream side and the downstream side of the annular nozzle 44 may shear the oversized agglomerates into subclumps that can pass through the annular gap 152. To combat the tendency for agglomerates to rapidly accumulate at a local agglomerate blockage, which may induce a self-propagating particle dam over the entire annular gap, the disperser pin 150 is rapidly dithered, or oscillated, along longitudinal axis 156. This movement fluidizes the particle dam and allows the local differential shear pressure to reduce individual agglomerate clumps so that they can pass through the annular nozzle 44. The disperser pin 150 is preferably dithered by stepper motor 200 at a frequency of about 1000 Hz and a displacement of about 0.0001 to about 0.0005 inch.

The dynamic shear force effect on particles in the dynamic shear region of annular nozzle 44 depends on the gas flow through the nozzle and the width of annular gap 180. The width of the annular gap will vary as a function of several factors, including initial tolerances, wear and particle buildup. Furthermore, the gas flow is likely to vary somewhat. As a result, a powder disperser with a fixed annular gap is likely to be subject to considerable variation in the dynamic shear force effect on particles of the powder sample.

In accordance with an important feature of the invention, a feedback control system 230 is used to dynamically control the width of the annular gap 180, thereby controlling the dynamic shear force applied to the aerosol transport gas, which in turn places reaction forces upon particles of the powder sample. The feedback control system 230 is best illustrated in FIG. 11. A differential pressure sensor 232 includes an upstream tap 234 for sensing the pressure in rapid acceleration chamber 40 and a downstream path 236 for sensing the pressure in convergence tube 47. It has been found that the differential pressure drop across the annular nozzle 44 is related to the parameters of the nozzle in accordance with the following equation:

$$DP = (Const \cdot DO^4 \cdot QA^4)/(KA^2 \cdot (DO-TA)^2 \cdot TA^6)$$

where DP is the differential pressure drop across the annular nozzle 44; QA is the gas flow throughput of the annular nozzle; KA is a variable geometry factor of the pin/bowl configuration; DO is the outer diameter of the annular gap 180 (inside diameter of the disperser bowl 152 at the annular flow nozzle); TA is the width of the annular gap 180; and Const is a unit conversion constant. Thus, from the measured differential pressure drop, the width of the annular gap 180 can be determined. The actual width of annular gap 180 is compared with a desired value, and an error is determined. An error signal is used to control stepper motor 200 so as to displace disperser pin 150 along longitudinal axis 156 in a direction to reduce the error.

The differential pressure drop across the annular nozzle can also be related only to the "pin-bowl" geometry and the stepper motor longitudinal drive motion position. This relationship has serious calibration drawbacks due to the necessity to know the pin-bowl annular nozzle dimension in absolute terms. This type of tight dimensional requirement puts a heavy burden on practical component machining tolerances. Another disadvantage to a purely geometrical base control system is that it does not compensate for part wear and thus dimensional degradation over a service time period.

As described above, the inside surface of disperser bowl 152 in the region of annular nozzle 44 has a linear slope, preferably about 7° with respect to longitudinal axis 156, thus providing a linear relationship between the width of annular gap 180 and displacement of disperser pin 150 along longitudinal axis 156. The feedback control system 230 provides dynamic control of the width of annular gap 180 and the dynamic shear force applied to the aerosol transport gas, which in turn places reaction forces upon the particles, within the annular nozzle 44. The dithering of disperser pin 150 along longitudinal axis 156 is relatively small in amplitude, and the differential pressure sensor 232 senses an average value of the pressure across the annular nozzle 44 as the disperser pin 150 is dithered.

Typically, the width of annular gap 180 can be set in a range between about 25 μm and 750 μm to accommodate particles of different sizes. The gap width is set to a desired value by controlling the stepper motor 200 to displace the disperser pin 150. The width of the annular gap 180 can be calibrated as a function of disperser pin position along longitudinal axis 156 by stroking the disperser pin 150 up and down and measuring the differential pressure drop with differential pressure sensor 232.

The local gas velocity of the annular nozzle 44 varies inversely with the width of annular gap 180. As the annular gap increases, the local throat velocity decreases and, conversely, as the annular gap decreases, the local throat velocity increases. Since the gas pressure drop in the form of shear force relates directly to the local gas velocity at the annular nozzle 44, the feedback control system provides dynamic control of the dynamic shear force.

Highly cohesive powder samples may produce built-up edges on the disperser pin 150 that propagate from the edge of annular gap 180 into the flow stream and reduce the original width of the annular gap. If left unattended, the annular gap can eventually be sealed by the particle buildup. The dithering of the disperser pin 150 inhibits the local deposition and buildup of residue particle edges and branches. When these occur, the growing branch or edge becomes unstable, breaks away from the vibrating pin body, and is broken up in the same manner as an oversized agglomerate.

The subclumps and particles that pass through the annular nozzle 44 are dispersed throughout the expanding discharge gas field downstream. The residual small agglomerates and subclumps are obliterated into their primary particle components through kinematic gas energy transfer in the form of dynamic gas forces acting upon individual agglomerate particles. The axial acceleration force and the lateral expansion force component of the expanding gas field spreads open the interstitial spaces between primary particles during the gas expansion process into the lower pressure discharge environment. The vector separation distance between primary particle centers can be increased or decreased as a function of the differential pressure across the annular nozzle 44. The greater the pressure drop, the greater the particle separation distance. For greater particle separation distances, the probability of interparticle collision and reagglomeration is lower.

The discharge aerosol gas is then compressed into the convergence tube 47 where the fully aerated dispersoid is reaccelerated into the tuned transport tube 45 for delivery to an instrument or process device. The immediate reacceleration of the pure dispersoid core flows particles away from the conduit walls, while maintaining the appropriate particle separation to prevent particle stackup and reagglomeration.

The control unit 13, which controls the powder disperser 11 and which supplies controlled gas flow for operation of the powder disperser 11, is shown in FIG. 11. The control unit includes a pneumatic support system and a microprocessor 300. A first pneumatic assembly 260 supplies pulsed gas for the pulsed gas jet 26. A second pneumatic assembly 262 supplies transport gas to the secondary chamber 30 as annular gas stream 88 and supplies the annular gas curtain 210 to rapid acceleration chamber 40. The microprocessor 300 controls the pneumatic assemblies 260 and 262 and the stepper motor 200.

The first pneumatic assembly 260 includes a compressor pump 264, typically having an operation range of 0.5 to 24 psia at 1–3 liters per minute. The output of compressor pump 264 is supplied to a pulsed jet valve 266 and to a dump valve 268. The output of pulsed jet valve 266 is supplied through conduit 94 to the fluidization assembly 14. The output of dump valve 268 is supplied through a diffuser 270 to the ambient. A pressure sensor 272 is connected to the compressor pump side of valve 266, and a pressure sensor 274 is connected to the pulsed jet side of valve 266. The pulsed jet valve 266 is a three-way valve controlled by pulse width modulation signal which determines the amount of gas jet pressure produced. The pressure across the valve 266 is monitored and controlled by the microprocessor 300. When the pulsed jet valve 266 is off, the pressure is relieved by the three-way valve to avoid pressure surges at turn-on. The dump valve 268 discharges the pulsed gas jet air supply into the ambient during the initial ramp-up of the cycle. By dumping most of the pump pressure and flow during start-up, the system is capable of achieving a precision gas jet pulse for accurate particle feed control. The dump valve 268 is ramped down until it is closed, as the requirement for greater gas jet feed pressure is ramped up by the ramping valve 266. The gas jet pulses supplied to the fluidization assembly 14 typically have a pulse width of about 0.5–1.0 second and a time between pulses of about 1–2 seconds, but are not limited to these ranges.

The second pneumatic assembly 262 includes an optional compressor pump 280, which preferably has an operating range of 5 to 17 psia at 15–17 liters per minute. The compressor pump 280 supplies the transport gas through conduit 128 and annular manifold 126 to the secondary chamber 30 as the annular transport gas stream 88. The output of compressor pump 280 is also connected to a flow control valve 282. The output of flow control valve 282 is supplied through conduit 163 to annular manifold 162. The annular gas curtain 210 is supplied from annular manifold 162 into rapid acceleration chamber 40 as described above. An optional flow restrictor 284 can be connected in parallel with flow control valve 282. The output of compressor pump 280 is also connected to a damping valve 286. The output of damping valve 286 is connected through a flow restrictor 288 and a diffuser 290 to the ambient.

The valves 266, 268, 282 and 286 are preferably solenoid valves having a response time on the order of 0.1 to 0.5 second. The stepper motor 200 can, for example, be a linear actuator 36000 series, supplied by HSI, Inc.

As shown in FIG. 11, the particle sizing system 12 typically includes a vacuum pump 292. In some cases, the vacuum pump 292 provides a sufficient flow of transport gas through the powder disperser and the compressor pump 280 is not required. The elevated transport air flow and pressure capacity provided by the compressor pump 280 benefits the powder dispersion function by providing a greater pressure drop across the annular nozzle 44. The elevated pressure drop greatly enhances the gas kinetic energy available for deagglomeration and controlled particle dispersion. In some cases, the particle morphology does not warrant a high energy dispersion process, and the vacuum pump 292 contained in the particle sizing system is sufficient.

When the pulsed gas jet 26 is injected into the primary chamber 22 and mixes with the transport gas flow, an additional flow and a pressure surge are superimposed on the closed system. In order to maintain more constant flow and pressure conditions, damping valve 286 is opened when the pulsed jet valve 266 is open, thus damping the pressure and flow surge into the system. By opening the damping valve 286, a portion of the transport air is discharged into the ambient.

The flow control valve 282 controls the flow through the momentum tube 18 by diverting more or less of the transport air from the secondary chamber 30. The valve 282 is used to control the velocity of the transport gas stream 208 through momentum tube 18. The flow control valve 282 supplies gas for the annular gas curtain 210 for protection of the disperser pin O-ring seal and particle downdraft guidance.

During operation, the flow rate through the powder disperser 11 is typically in a range of 15 to 17 liters per minute, and the pressure is typically in a range of 0.5 to 12.5 psi when the compressor pump 280 is used. The pressure and flow rate are adjusted to permit efficient fluidization and dispersion of the powder sample being processed. It has been found that a pressure of about 7 psi is suitable for dispersion of about 90% of all powders.

In summary, the fluidization assembly 14 is provided with two incoming gas sources: (1) the pulsed gas jet 26 through conduit 128, and (2) the transport gas through conduit 94. The pulsed gas jet 26 fluidizes and reduces agglomerates in the powder sample 24 by a pulsed jet impingement process. The transport gas entrains the coarse aerosol in the secondary chamber 30 and accelerates it for further reduction by controlled impaction and deagglomeration in the dynamic shear dispersion assembly 16.

The dynamic shear dispersion assembly 16 also has two incoming gas sources: (1) the particle transport gas stream 208 through momentum tube 18, and (2) the annular gas curtain 210 which is supplied through conduit 163. The transport gas stream 208 accelerates particles and agglomerates by gas momentum transfer for deagglomeration by impingement on impact surface 42 of disperser pin 150. The annular gas curtain 210 provides a protective sheath for the disperser pin dynamic O-ring seal 158 and provides a source of continuous downdraft air to assist in rapid entrainment of deagglomerated particles. The deagglomerated particles are further reduced within the high shear flow field of the annular nozzle 44. The high energy expanding gas discharge separates and aerates the remaining agglomerates into a fully dispersed aerosol. The emerging dispersoid is then reaccelerated for transport to an analytical instrument or a powder processing device.

The microprocessor 300 receives inputs from the differential pressure sensor 232 and the pressure sensors 272 and 274. Microprocessor 300 supplies control signals in accordance with the operation described above to stepper motor 200, pulsed jet valve 266, dump valve 268, flow control valve 282 and damping valve 286. In one example, the microprocessor 300 is a Motorola 68000 series microprocessor.

The powder dispersion system also incorporates feedback control of the rate of particle feed to the particle sizing system 120. The particle feed rate is preferably adjustable in a range of about 500 to 80,000 particles per second. The particle sizing system 12 senses the particle feed rate and provides an error signal which is used to control the peak pressure of the pulse gas jet 26 (by controlling valve 266). By increasing the pressure of the pulse gas jet, the particle feed rate is increased, and, conversely, the particle feed rate is decreased by decreasing the pressure of the pulse gas jet.

In some instances, the particles to be dispersed and analyzed may be available in the form of a continuous stream rather than a powder sample. For example, it may be desired to monitor particles in a process line. In this case, the fluidization assembly 14 is omitted from the powder disperser 11, and the particle stream is fed directly into the momentum tube 18 for processing in the dynamic shear dispersion assembly 16.

While there have been shown and described what are at present considered the preferred embodiments of the present invention, it will be obvious to those skilled in the art that various changes and modifications may be made therein without departing from the scope of the invention as defined by the appended claims.

What is claimed is:

1. Apparatus for dispersion of particles in a gas, comprising:

a structure defining a rapid acceleration chamber, a momentum tube for supplying particles to said rapid acceleration chamber and an annular nozzle at an outlet of said rapid acceleration chamber for dynamic shear dispersion of said particles, said structure comprising a housing and a disperser pin mounted within said housing, said disperser pin having a longitudinal axis, said rapid acceleration chamber containing an impact surface for impingement and deagglomeration of particles that are received through said momentum tube, said impact surface and said momentum tube being configured such that said particles received from said momentum tube impinge on said impact surface at a tangential grazing angle, said impact surface being formed on said disperser pin and said momentum tube being offset from the longitudinal axis of said disperser pin; and means for supplying a gas stream through said rapid acceleration chamber between said impact surface and said annular nozzle for rapidly accelerating said particles between said impact surface and said annular nozzle.

2. Apparatus for dispersion of particles in a gas, comprising:

a structure defining a rapid acceleration chamber, a momentum tube for supplying particles to said rapid acceleration chamber and an annular nozzle at an outlet of said rapid acceleration chamber for dynamic shear dispersion of said particles, said structure comprising a housing and a disperser pin mounted within said housing, said disperser pin having a longitudinal axis, said rapid acceleration chamber containing an impact surface for impingement and deagglomeration of particles that are received through said momentum tube, said impact surface being concave in a plane that contains said longitudinal axis and being convex in a plane perpendicular to said longitudinal axis; and means for supplying a gas stream through said rapid acceleration chamber between said impact surface and said annular nozzle for rapidly accelerating said particles between said impact surface and said annular nozzle.

3. Apparatus for dispersion of particles in a gas, comprising:

a structure defining a rapid acceleration chamber, a momentum tube for supplying particles to said rapid acceleration chamber and an annular nozzle at an outlet of said rapid acceleration chamber for dynamic shear dispersion of said particles, said structure comprising a housing and a disperser pin mounted within said housing, said disperser pin having a longitudinal axis, said rapid acceleration chamber containing an impact surface for impingement and deagglomeration of particles that are received through said momentum tube;

means for supplying a gas stream through said rapid acceleration chamber between said impact surface and said annular nozzle for rapidly accelerating said particles between said impact surface and said annular nozzle; and means for mechanically dithering said annular nozzle such that said annular nozzle tends to remain free from particle buildup, said means for mechanically dithering said annular nozzle comprising an actuator coupled to said disperser pin for translating said disperser pin along said longitudinal axis relative to said housing with an oscillatory motion.

4. Apparatus as defined in claim 3 wherein said impact surface and said momentum tube are configured such that said particles received from said momentum tube impinge on said impact surface at a tangential grazing angle.

5. Apparatus as defined in claim 4 wherein said impact surface is formed on said disperser pin and wherein said momentum tube is offset from the longitudinal axis of said disperser pin.

6. Apparatus as defined in claim 3 wherein said impact surface is formed on said disperser pin and further including means for rotating said disperser pin relative to said momentum tube.

7. Apparatus as defined in claim 3 wherein said impact surface is concave in a plane that contains said longitudinal axis and is convex in a plane perpendicular to said longitudinal axis.

8. Apparatus as defined in claim 3 wherein said gas stream comprises an annular gas curtain through said rapid acceleration chamber and a transport gas stream through said momentum tube and said rapid acceleration chamber.

9. Apparatus as defined in claim 8 wherein said particles pass through said annular gas curtain before impingement on said impact surface.

10. Apparatus as defined in claim 8 further including means for controlling the velocity of the transport gas stream through said momentum tube.

11. Apparatus as defined in claim 8 wherein said housing and said disperser pin define an annular manifold for supplying said annular gas curtain and an annular gap for carrying said annular gas curtain from said annular manifold into said rapid acceleration chamber.

12. Apparatus as defined in claim 3 wherein said rapid acceleration chamber includes a cylindrical sidewall defined by said housing, a continuously curved surface of said disperser pin between said impact surface and said annular nozzle and a surface of said housing between said sidewall and said annular nozzle, said rapid acceleration chamber having circular symmetry about said longitudinal axis.

13. Apparatus as defined in claim 3 wherein said momentum tube is defined by said housing and is inclined with respect to said longitudinal axis at an angle in a range of about 35° to 47°.

14. Apparatus as defined in claim 3 wherein said momentum tube is inclined at an angle of about 45° with respect to said longitudinal axis.

15. Apparatus as defined in claim 3 wherein said annular nozzle includes an annular gap and wherein said means for translating said disperser pin causes the width of the annular gap in said annular nozzle to be varied.

16. Apparatus as defined in claim 3 wherein said housing further defines a divergence tube downstream of said annular nozzle and a convergence tube downstream of said divergence tube.

17. Apparatus as defined in claim 16 wherein a tapered portion of said disperser pin extends into said divergence tube along said longitudinal axis.

18. Apparatus as defined in claim 3 wherein a dynamic shear force is applied to said gas stream within said annular nozzle, further including feedback means for dynamically controlling the dynamic shear force on said gas stream, which in turn places reaction forces upon particles, within said annular nozzle.

19. Apparatus as defined in claim 18 wherein said annular nozzle includes an annular gap and wherein said feedback means comprises gap control means for dynamically controlling the width of said annular gap.

20. Apparatus as defined in claim 19 wherein said gap control means comprises:
  means for sensing a differential pressure across said annular nozzle;
  means responsive to the difference between the sensed differential pressure and a desired value of said differential pressure for determining an error in said differential pressure, and
  means responsive to said error for varying said annular gap so as to reduce said error.

21. Apparatus as defined in claim 20 wherein said means for varying said annular gap comprises means for displacing said disperser pin along said longitudinal axis relative to said housing.

22. Apparatus as defined in claim 19 wherein said annular gap is defined between a sharp circular ridge on said disperser pin and a truncated conical inside surface of said housing.

23. Apparatus as defined in claim 3 further including a fluidization assembly for fluidizing a powder sample into particles and for entraining said particles in a transport gas stream flowing through said momentum tube.

24. Apparatus as defined in claim 23 wherein said fluidization assembly comprises:
  a primary chamber for holding said powder sample, said primary chamber having an upper end,
  a secondary chamber for mixing particles of said powder sample with said transport gas stream, said secondary chamber being located above said primary chamber, said primary and secondary chambers being connected by an opening in the upper end of said primary chamber, said momentum tube being connected to said secondary chamber,
  means for directing a pulsed gas jet through said opening into said primary chamber for dispersing said particles of said powder sample into said secondary chamber, and
  means for directing said transport gas stream through said secondary chamber for transporting said particles from said secondary chamber through said momentum tube.

25. Apparatus as defined in claim 24 wherein the upper end of said primary chamber is substantially hemispherical in shape and wherein said primary chamber includes a lower end having a substantially hemispherical shape.

26. Apparatus as defined in claim 24 wherein said secondary chamber has a conical lower end centered on said opening so that particles not transported through said momentum tube fall back through said opening into said primary chamber.

27. Apparatus as defined in claim 26 wherein said means for directing said pulsed gas jet comprises a gas jet nozzle located at an upper end of said secondary chamber for directing said pulsed gas jet into said primary chamber, said gas jet nozzle having a continuously curved outer surface.

28. Apparatus as defined in claim 24 wherein means for directing said pulsed gas jet includes means for directing a plurality of gas pulses into said primary chamber, with said gas pulses successively increasing in pressure until a desired pressure is reached.

29. Apparatus as defined in claim 24 wherein said transport gas stream has an annular flow into said secondary chamber, thereby causing a toroidal vortex swirl within said secondary chamber for entraining said particles into said transport gas stream.

30. Apparatus for fluidization of a powder sample into a gas stream, comprising:
  a primary chamber for holding a powder sample, said primary chamber having an upper end;
  a secondary chamber located above said primary chamber, said primary and secondary chambers being connected by an opening in the upper end of said primary chamber;
  means for directing a pulsed gas jet through said opening into said primary chamber for dispersing said particles of said powder sample into said secondary chamber through said opening between said primary and secondary chambers;
  a momentum tube coupled to said secondary chamber; and means for directing a transport gas stream independent of said pulsed gas jet through said secondary chamber, said transport gas stream mixing with said particles of said powder sample in said secondary chamber and transporting said particles from said secondary chamber through said momentum tube.

31. Apparatus as defined in claim 30 wherein the upper end of said primary chamber is substantially hemispherical in shape and wherein said primary chamber includes a lower end having a substantially hemispherical shape.

32. Apparatus as defined in claim 30 wherein said secondary chamber has a conical lower end centered on said opening so that particles not transported through said momentum tube fall back through said opening into said primary chamber.

33. Apparatus as defined in claim 30 wherein said means for directing said pulsed gas jet includes means for directing a plurality of gas pulses into said secondary chamber, with said gas pulses successively increasing in pressure until a desired pressure is reached.

34. Apparatus as defined in claim 30 wherein said means for directing said pulsed gas jet comprises a nozzle located at an upper end of said secondary chamber for directing said pulsed gas jet into said primary chamber, said nozzle having a continuously curved outer surface.

35. Apparatus as defined in claim 34 wherein said transport gas has an annular flow into said secondary chamber, thereby causing a toroidal vortex swirl within said secondary chamber for entraining said particles into said transport gas.

36. Apparatus as defined in claim 30 further including an assembly coupled to said momentum tube for dynamic shear dispersion of said particles carried through said momentum tube.

37. Apparatus as defined in claim 30 wherein said primary chamber is defined by a removable sample cup, said sample cup including a base for receiving said powder sample and a cap having said opening.

38. Apparatus as defined in claim 37 further including means for grounding said sample cup so as to reduce static charge on said powder sample.

39. Apparatus for dispersion of particles in a gas, comprising:
- a dynamic shear dispersion nozzle including an annular gap for dynamic shear dispersion of said particles;
- a first conduit located upstream of said dynamic shear dispersion nozzle, said first conduit having an inlet for receiving particles;
- a second conduit located downstream of said dynamic shear dispersion nozzle;
- means for supplying a transport gas stream through said first conduit and said dynamic shear dispersion nozzle to said second conduit for transporting said particles through said dynamic shear dispersion nozzle; and
- feedback means for dynamically controlling the dynamic shear force on the transport gas stream, which in turn places reaction forces upon said particles, within said dynamic shear dispersion nozzle, said feedback means comprising gap control means for dynamically controlling the width of said annular gap.

40. Apparatus as defined in claim 39 wherein said gap control means comprises:
- means for sensing a differential pressure across said dynamic shear dispersion nozzle,
- means responsive to the difference between the sensed differential pressure and a desired value of said differential pressure for determining an error in said differential pressure, and
- means responsive to said error for varying said annular gap so as to reduce said error.

41. Apparatus as defined in claim 40 wherein said annular gap is defined between a housing and a disperser pin and wherein said means for varying said annular gap comprises means for displacing said disperser pin relative to said housing.

42. Apparatus for dispersion of particles in a gas, comprising:
- a primary chamber for holding a powder sample, said primary chamber having an upper end;
- a secondary chamber for mixing particles of said powder sample with a transport gas stream, said secondary chamber being located above said primary chamber, said primary and secondary chambers being connected by an opening in the upper end of said primary chamber;
- means for directing a pulsed gas jet through said opening into said primary chamber for dispersing said particles of said powder sample into said secondary chamber;
- a momentum tube coupled at one end to said secondary chamber for carrying said transport gas stream and said particles from said secondary chamber;
- an impact surface disposed at the other end of said momentum tube for impingement and deagglomeration of particles that are transported through said momentum tube from said secondary chamber;
- an annular nozzle for dynamic shear dispersion of said particles, said annular nozzle having an annular gap;
- a rapid acceleration chamber for rapidly accelerating said particles between said impact surface and said annular nozzle;
- means for dithering the annular gap of said annular nozzle such that said annular nozzle tends to remain free from particle buildup; and
- means for directing said transport gas stream through said secondary chamber, said momentum tube, said rapid acceleration chamber and said annular nozzle.

43. An apparatus as defined in claim 42 further including a divergence tube downstream of said annular nozzle and a convergence tube downstream of said divergence tube.

44. Apparatus as defined in claim 42 further including feedback means for dynamically controlling the dynamic shear force on the transport gas stream, which in turn places reaction forces upon said particles, within said annular nozzle.

45. Apparatus as defined in claim 42 further including means for dynamically controlling the annular gap of the annular nozzle by longitudinal displacement of the disperser pin.

46. Apparatus for dispersion of particles in a gas, comprising:
- a structure defining a rapid acceleration chamber, a momentum tube for supplying particles to said rapid acceleration chamber and an annular nozzle at an outlet of said rapid acceleration chamber for dynamic shear dispersion of said particles, said structure comprising a housing and a disperser pin mounted within said housing, said rapid acceleration chamber containing an impact surface for impingement and deagglomeration of particles that are received through said momentum tube; and
- means for supplying a gas stream through said rapid acceleration chamber between said impact surface and said annular nozzle for rapidly accelerating said particles between said impact surface and said annular nozzle, said gas stream comprising an annular gas curtain through said rapid acceleration chamber and a transport gas stream through said momentum tube and said rapid acceleration chamber.

47. Apparatus for dispersion of particles in a gas, comprising:
- a structure defining a rapid acceleration chamber, a momentum tube for supplying particles to said rapid acceleration chamber and an annular nozzle at an outlet of said rapid acceleration chamber for dynamic shear dispersion of said particles, said structure comprising a housing and a disperser pin mounted within said housing, said disperser pin having a longitudinal axis, said rapid acceleration chamber containing an impact surface for impingement and deagglomeration of particles that are received through said momentum tube, said rapid acceleration chamber including a cylindrical sidewall defined by said housing, a continuously curved surface of said disperser pin between said impact surface and said annular nozzle and a surface of said housing between said sidewall and said annular nozzle, said rapid acceleration chamber having circular symmetry about said longitudinal axis; and means for supplying a gas stream through said rapid acceleration chamber between said impact surface and said annular nozzle for rapidly accelerating said particles between said impact surface and said annular nozzle.

48. Apparatus for dispersion of particles in a gas, comprising:

a structure defining a rapid acceleration chamber, a momentum tube for supplying particles to said rapid acceleration chamber and an annular nozzle at an outlet of said rapid acceleration chamber for dynamic shear dispersion of said particles, said structure comprising a housing and a disperser pin mounted within said housing, said disperser pin having a longitudinal axis, said disperser pin having an impact surface for impingement and deagglomeration of particles that are received through said momentum tube, said impact surface being curved and being oriented relative to said momentum tube to avoid perpendicular impingement of particles received through said momentum tube on said impact surface; and means for supplying a gas stream through said rapid acceleration chamber between said impact surface and said annular nozzle for rapidly accelerating said particles between said impact surface and said annular nozzle.

\* \* \* \* \*